(12) United States Patent
Murakami et al.

(10) Patent No.: US 12,727,748 B2
(45) Date of Patent: Sep. 8, 2026

(54) ENDOSCOPE SYSTEM AND TREATMENT METHOD ENDOSCOPIC TREATMENT TOOL

(71) Applicant: OLYMPUS CORPORATION, Tokyo (JP)

(72) Inventors: Kenji Murakami, Hino (JP); Genri Inagaki, Fuchu (JP); Ryohei Ogawa, Kokubunji (JP); Hidetoshi Nishimura, Koganei (JP); Takashi Otawara, Hachioji (JP); Yuji Sakamoto, Kunitachi (JP); Shintaro Inoue, Westborough, MA (US)

(73) Assignee: OLYMPUS CORPORATION, Tokyo (JP)

( * ) Notice: Subject to any disclaimer, the term of this patent is extended or adjusted under 35 U.S.C. 154(b) by 195 days.

(21) Appl. No.: 18/621,337

(22) Filed: Mar. 29, 2024

(65) Prior Publication Data

US 2024/0324865 A1 Oct. 3, 2024

Related U.S. Application Data

(60) Provisional application No. 63/456,050, filed on Mar. 31, 2023.

(51) Int. Cl.
*A61B 1/04* (2006.01)
*A61B 1/00* (2006.01)

(52) U.S. Cl.
CPC .......... *A61B 1/042* (2013.01); *A61B 1/00006* (2013.01); *A61B 1/00087* (2013.01); *A61B 1/00094* (2013.01); *A61B 1/00133* (2013.01)

(58) Field of Classification Search
None
See application file for complete search history.

(56) References Cited

U.S. PATENT DOCUMENTS

| | | | | |
|---|---|---|---|---|
| 12,127,890 | B1 * | 10/2024 | Gorrepati | A61B 34/25 |
| 2003/0055315 | A1 * | 3/2003 | Gatto | A61B 1/00126 600/114 |
| 2003/0078473 | A1 * | 4/2003 | Richardson | A61M 25/0069 600/207 |
| 2003/0181823 | A1 * | 9/2003 | Gatto | A61B 1/3132 600/564 |
| 2003/0187319 | A1 * | 10/2003 | Kaneko | A61N 2/00 600/9 |

(Continued)

*Primary Examiner* — Mohammad J Rahman
(74) *Attorney, Agent, or Firm* — Scully, Scott, Murphy & Presser, P.C.

(57) ABSTRACT

An endoscope system includes a direct-view endoscope configured to capture images, a treatment tool configured to be inserted into the endoscope, and a controller comprising hardware, the controller being configured to control a drive device to drive the endoscope and the treatment tool, to control driving of the endoscope to locate the endoscope inserted into a lumen in the vicinity of a nipple, to control driving of the treatment tool to move the nipple using the treatment tool, to acquire a first captured image of the nipple from the endoscope, and to predict a shape of a biliary duct connected to the nipple in the first captured image based on biliary duct shape information comprising a standard image of the nipple that is associated with a standard shape of the biliary duct.

13 Claims, 13 Drawing Sheets

(56) References Cited

U.S. PATENT DOCUMENTS

| | | | | |
|---|---|---|---|---|
| 2003/0187324 | A1* | 10/2003 | Gatto | A61B 10/0041 600/101 |
| 2003/0187427 | A1* | 10/2003 | Gatto | A61B 5/417 600/101 |
| 2006/0270900 | A1* | 11/2006 | Chin | A61B 1/313 606/1 |
| 2009/0105534 | A1* | 4/2009 | Nakagawa | A61B 1/018 600/106 |
| 2013/0211246 | A1* | 8/2013 | Parasher | A61B 1/0638 600/431 |
| 2020/0030575 | A1 | 1/2020 | Bogusky et al. | |
| 2020/0100655 | A1* | 4/2020 | Morishima | A61B 1/053 |
| 2020/0305834 | A1* | 10/2020 | Uchihara | A61B 8/469 |
| 2022/0087513 | A1* | 3/2022 | Dejima | A61B 18/1492 |
| 2022/0192470 | A1* | 6/2022 | Makino | A61B 1/00045 |
| 2023/0142219 | A1* | 5/2023 | Makino | A61B 1/000094 382/128 |

* cited by examiner

300
DRIVE DEVICE
360
DRIVE CONTROLLER
361
PROCESSOR
364
INPUT/OUTPUT CONTROL UNIT
400
VIDEO CONTROL DEVICE
460
MAIN CONTROLLER
461
PROCESSOR
462
MEMORY
463
STORAGE UNIT
464
INPUT/OUTPUT CONTROL UNIT
420
IMAGING PROCESSING UNIT
430
LIGHT SOURCE UNIT
410
ENDOSCOPE ADAPTER
173
174
1502(150)
SECOND ATTACHMENT/ DETACHMENT PORTION
900
DISPLAY DEVICE

ENDOSCOPE SYSTEM AND TREATMENT METHOD ENDOSCOPIC TREATMENT TOOL

CROSS-REFERENCE TO RELATED APPLICATIONS

The present application claims priority based on U.S. Patent Provisional Application No. 63/456,050 filed in the United States on Mar. 31, 2023, the contents of which are incorporated herein by reference.

BACKGROUND

Technical Field

The present disclosure relates to an endoscope system and a treatment method.

Description of Related Art

A side-view flexible endoscope is used for endoscopic retrograde cholangiopancreatography (ERCP). On the other hand, when reconstructive surgery has been performed in a part of a path through which a flexible endoscope passes, the path may be complicated. In this case, a direct-view flexible endoscope which can be more easily inserted into a complicated path in comparison with the side-view flexible endoscope is used for ERCP.

United States Patent Application, Publication No. 2020/0030575 (Patent Document 1) discloses a medical system in which a cannula is automatically inserted into a nipple.

SUMMARY

However, when ERCP is performed using a direct-view flexible endoscope, it is necessary to ascertain a nipple of a biliary duct from the front by greatly curving the direct-view flexible endoscope or the like.

In consideration of the aforementioned circumstances, an objective of the present disclosure is to provide an endoscope system and a treatment method that can easily ascertain a nipple of a biliary duct from the front.

In order to achieve the objective, the present disclosure employs the following means.

According to a first aspect of the present disclosure, there is provided an endoscope system comprising: a direct-view endoscope configured to capture images a treatment tool configured to be inserted into the endoscope; and a controller comprising hardware, the controller being configured to: control a drive device to drive the endoscope and the treatment tool; control driving of the endoscope to locate the endoscope inserted into a lumen in the vicinity of a nipple, control driving of the treatment tool to move the nipple using the treatment tool, acquire a first captured image of the nipple from the endoscope, and predict a shape of a biliary duct connected to the nipple in the first captured image based on biliary duct shape information comprising a standard image of the nipple that is associated with a standard shape of the biliary duct.

According to a second aspect of the present disclosure, there is provided a treatment method of treating a biliary duct, locating an endoscope inserted into a lumen in the vicinity of a nipple; moving the nipple using a treatment tool (inserted into the endoscope; acquiring a first captured image of the nipple from the endoscope; and predicting a shape of the biliary duct connected to the nipple in the first captured image based on biliary duct shape information comprising a standard image of the nipple that is associated with a standard shape of the biliary duct.

With the endoscope system and the treatment method according to the present disclosure, it is possible to easily ascertain a nipple of a biliary duct from the front of a direct-view flexible endoscope.

DETAILED DESCRIPTION

First Embodiment

Figure 1:
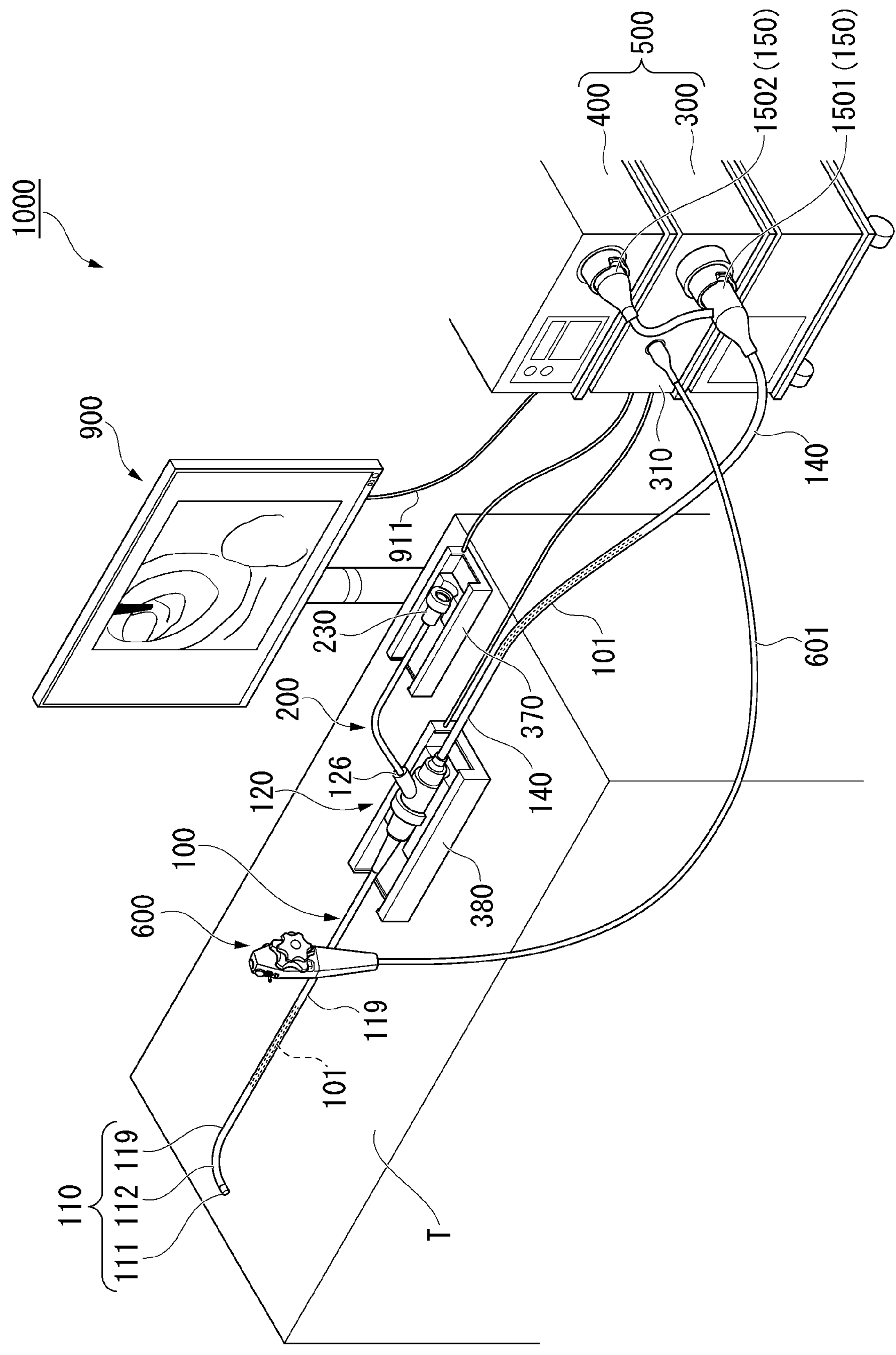
FIG. 1 is a diagram illustrating the entire configuration of an endoscope system according to a first embodiment.

An endoscope system 1000 according to a first embodiment of the present disclosure will be described below with reference to FIGS. 1 to 15. FIG. 1 is a diagram illustrating the entire configuration of the endoscope system 1000.

Endoscope System 1000

The endoscope system 1000 is a medical system that observes and treats an internal part of a patient lying on an operating table T. The endoscope system 1000 includes an endoscope 100, an endoscopic treatment tool 200, a drive device 300, a video control device 400, an operation device 600, an observation device 700, and a display device 900.

The endoscope 100 is a device that is inserted into a lumen of a patient to observe and treat a lesion. The endoscope 100 is detachably attached to the drive device 300 and the video control device 400. An internal path 101 is formed in the endoscope 100. In the following description, a side of the endoscope 100 which is inserted into a lumen of a patient is referred to as a "distal end side A1," and a side which is attached to the drive device 300 is referred to as a "proximal end side A2."

As illustrated in FIG. 1, the endoscopic treatment tool 200 is inserted into the internal path 101 of the endoscope 100 via a forceps port 126 provided in a connection portion 120 of the endoscope 100. A forceps 210 (see FIG. 2) is provided at a distal end of the endoscopic treatment tool 200. An operation portion 230 that operates the forceps 210 is provided at a proximal end of the endoscopic treatment tool 200.

The drive device 300 is detachably connected to the endoscope 100 and the operation device 600. The drive device 300 drives a built-in motor to electrically drive the endoscope 100 on the basis of an operation input to the operation device 600. The drive device 300 drives a built-in pump or the like to cause the endoscope 100 to perform air supply/suction on the basis of an operation input to the operation device 600.

The drive device 300 includes a treatment tool drive device 370 to which the operation portion 240 of the endoscopic treatment tool 200 is detachably connected and a connection portion drive device 380 to which the connection portion 120 of the endoscope 100 is detachably connected.

The video control device 400 is detachably connected to the endoscope 100 and acquires a captured image from the endoscope 100. The video control device 400 displays the captured image acquired from the endoscope 100 or a GUI image or a CG image for providing information to an operator on the display device 900.

The drive device 300 and the video control device 400 constitute a control device 500 that controls the endoscope system 1000. The control device 500 may further include a peripheral such as a video printer. The drive device 300 and the video control device 400 may be an integrated device.

The operation device 600 is detachably connected to the drive device 300 via an operation cable 601. The operation device 600 may be able to communicate with the drive device 300 by wireless communication instead of wired communication. An operator can electrically drive the endoscope 100 by operating the operation device 600.

The display device 900 is a device that can display an image such as an LCD. The display device 900 is connected to the video control device 400 via a display cable 911.

The constituent devices of the endoscope system 1000 will be described below in detail.

Endoscope 100

The endoscope 100 is a direct-view flexible endoscope and includes an insertion portion 110, a connection portion 120, an in-vitro flexible portion 140, an attachment/detachment portion 150, a curved wire 160, and a built-in element 170.

Figure 2:
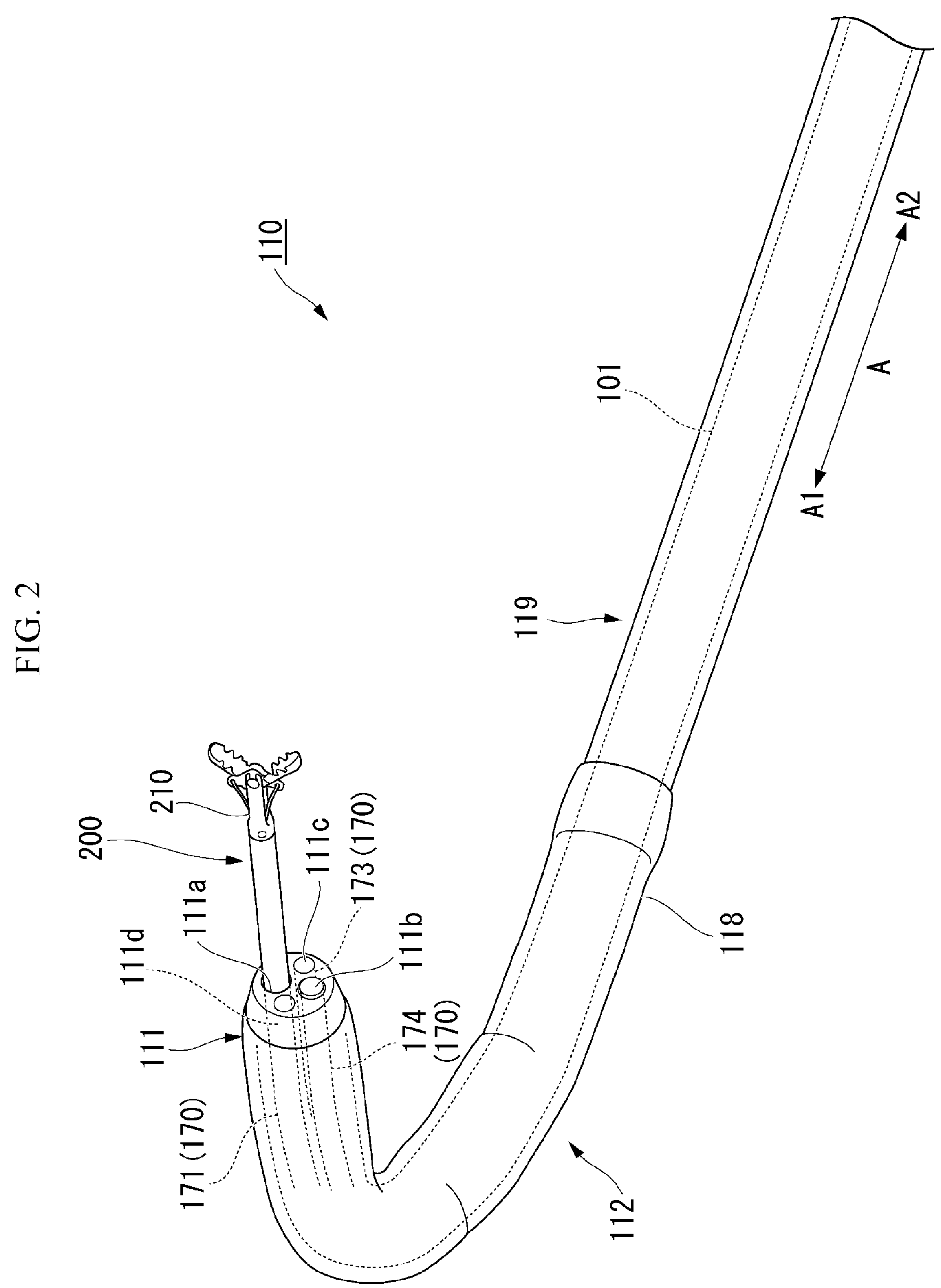
FIG. 2 is a diagram illustrating an insertion portion of an endoscope of the endoscope system.

FIG. 2 is a diagram illustrating the insertion portion 110 of the endoscope 100.

An internal path 101 extending in a length direction A of the endoscope 100 from the distal end of the insertion portion 110 to the proximal end is formed in the endoscope 100. The curved wire 160 and the built-in element 170 are inserted into the internal path 101. The curved wire 160 includes an operating wire for curving a curved portion 112. The built-in element 170 includes a channel tube 171, an imaging cable 173, and a light guide 174.

Insertion Portion 110

The insertion portion 110 is a thin longitudinal member that can be inserted to a lumen. The insertion portion 110 includes a distal end portion 111, a curved portion 112, and an in-vivo flexible portion 119. The distal end portion 111, the curved portion 112, and the in-vivo flexible portion 119 are sequentially connected from the distal end side.

The distal end portion 111 is formed in a substantially cylindrical shape out of a metal or the like. The distal end portion 111 includes an opening portion 111*a*, an illumination portion 111*b*, and an imaging portion 111*c*. The opening portion 111*a* is an opening communicating with the channel tube 171. As illustrated in FIG. 2, the endoscopic treatment tool 200 inserted into the channel tube 171 protrudes from or retracts into the opening portion 111*a*.

The illumination portion 111*b* is connected to the light guide 174 that guides illumination light and emits illumination light for illuminating an imaging target. The imaging portion 111*c* includes an imaging element such as a CMOS and images an imaging target. An imaging signal is sent to the video control device 400 via the imaging cable 173.

The curved portion 112 can be curved in a vertical direction (also referred to as a "UD direction") perpendicular to the length direction A or a lateral direction (also referred to as an "LR direction") perpendicular to the length direction A and the UD direction. A distal end of the operating wire is fixed to the distal end side of the curved portion 112. The operating wire extends to the attachment/detachment portion 150 via the internal path 101.

The in-vivo flexible portion 119 is a long and flexible tubular member. The curved wire 160, the channel tube 171, the imaging cable 173, and the light guide 174 are inserted into the internal path 101 formed in the in-vivo flexible portion 119.

Connection Portion 120

Figure 3:
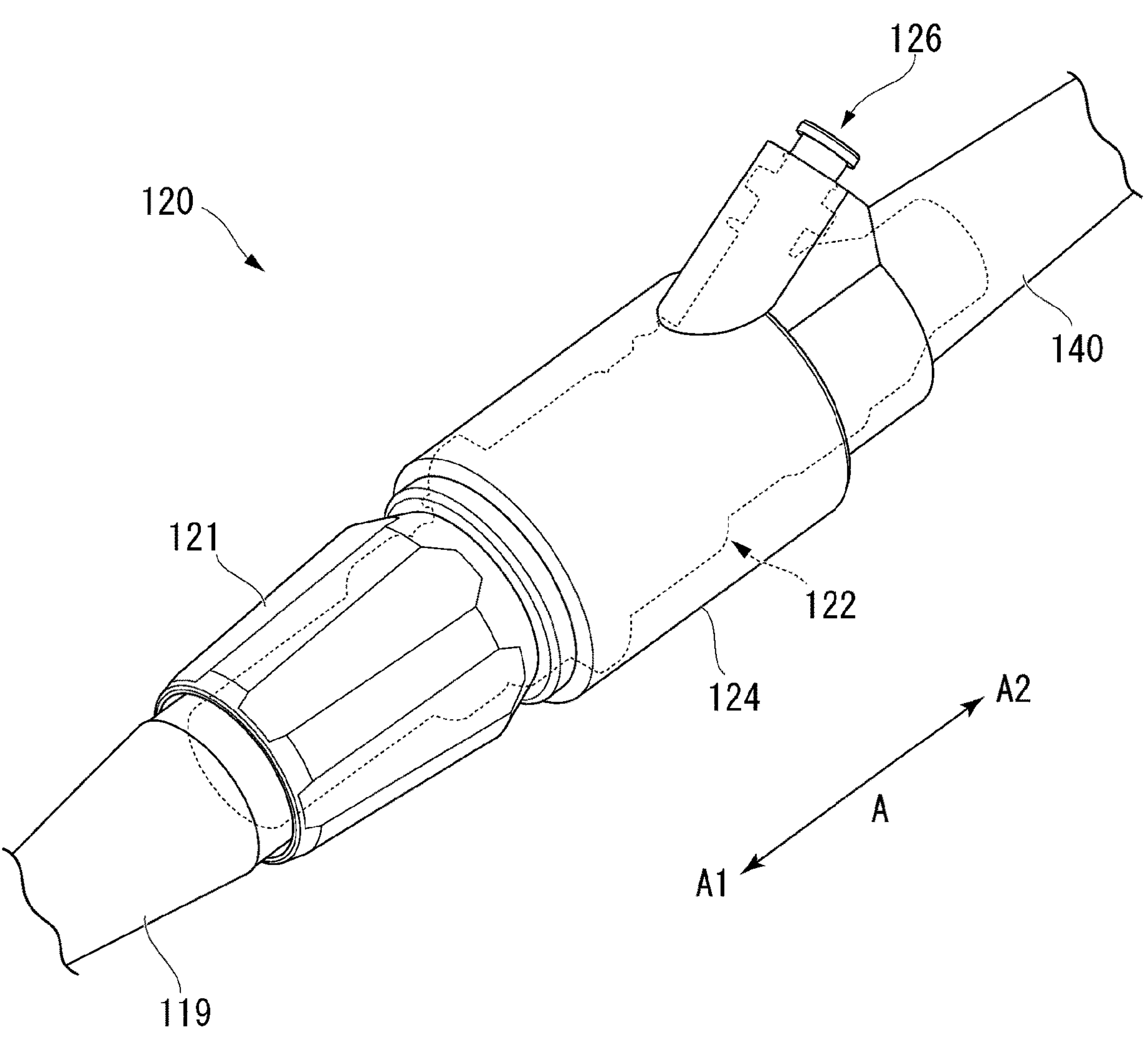
FIG. 3 is a perspective view of a connection portion of the endoscope.

FIG. 3 is a perspective view of the connection portion 120.

The connection portion 120 is a member that connects the in-vivo flexible portion 119 of the insertion portion 110 and the in-vitro flexible portion 140. The connection portion 120 includes a cylindrical member 121, a connection portion body 122, a bearing portion 124, and a forceps port 126.

The cylindrical member 121 is formed in a cylindrical shape. An internal space of the cylindrical member 121 communicates with an internal space of the in-vivo flexible portion 119 and forms a part of the internal path 101. The curved wire 160, the channel tube 171, the imaging cable 173, and the light guide 174 are inserted into the internal space of the cylindrical member 121.

The connection portion body 122 is formed in a substantially cylindrical shape. The cylindrical member 121 is inserted into a distal end opening of the connection portion body 122. An internal space of the connection portion body 122 communicates with the internal space of the in-vitro flexible portion 140 and forms a part of the internal path 101.

The bearing portion 124 connects the connection portion body 122 and the cylindrical member 121 such that they can rotate about a rotation axis extending in the length direction A. Specifically, the bearing portion 124 is fixed to the connection portion body 122. The bearing portion 124 supports the cylindrical member 121 such that it can rotate about a rotation axis extending in the length direction A.

The in-vivo flexible portion 119 is fixed to the cylindrical member 121. Accordingly, the in-vivo flexible portion 119 and the cylindrical member 121 rotate integrally (hereinafter also referred to as "roll and rotate") relative to the connection portion body 122.

The forceps port 126 is an insertion port into which the endoscopic treatment tool 200 is inserted. The forceps port 126 is formed in a cylindrical shape.

The in-vivo flexible portion 119 and the in-vitro flexible portion 140 are connected to be rotatable about a rotation axis extending in the length direction A by the connection portion 120. Accordingly, when an operator rotates the in-vivo flexible portion 119 of the insertion portion 110 about a rotation axis extending in the length direction A, it is possible to rotate only the in-vivo flexible portion 119 without rotating the in-vitro flexible portion 140 extending to the vicinity of the drive device 300.

In-Vitro Flexible Portion 140

The in-vitro flexible portion 140 is a long tubular member. The curved wire 160, the imaging cable 173, the light guide 174, and an air supply/suction tube 172 (see FIG. 5) are inserted into the internal path 101 formed in the in-vitro flexible portion 140. The air supply/suction tube 172 is connected to the channel tube 171.

Attachment/Detachment Portion 150

As illustrated in FIG. 1, the attachment/detachment portion 150 includes a first attachment/detachment portion 1501 attached to the drive device 300 and a second attachment/detachment portion 1502 attached to the video control device 400. The first attachment/detachment portion 1501 and the second attachment/detachment portion 1502 may be an integrated attachment/detachment portion.

The internal path 101 formed in the in-vitro flexible portion 140 branches to the first attachment/detachment portion 1501 and the second attachment/detachment portion 1502. The curved wire 160 and the air supply/suction tube 172 are inserted into the first attachment/detachment portion 1501. The imaging cable 173 and the light guide 174 are inserted into the second attachment/detachment portion 1502.

Drive Device 300

Figure 4:
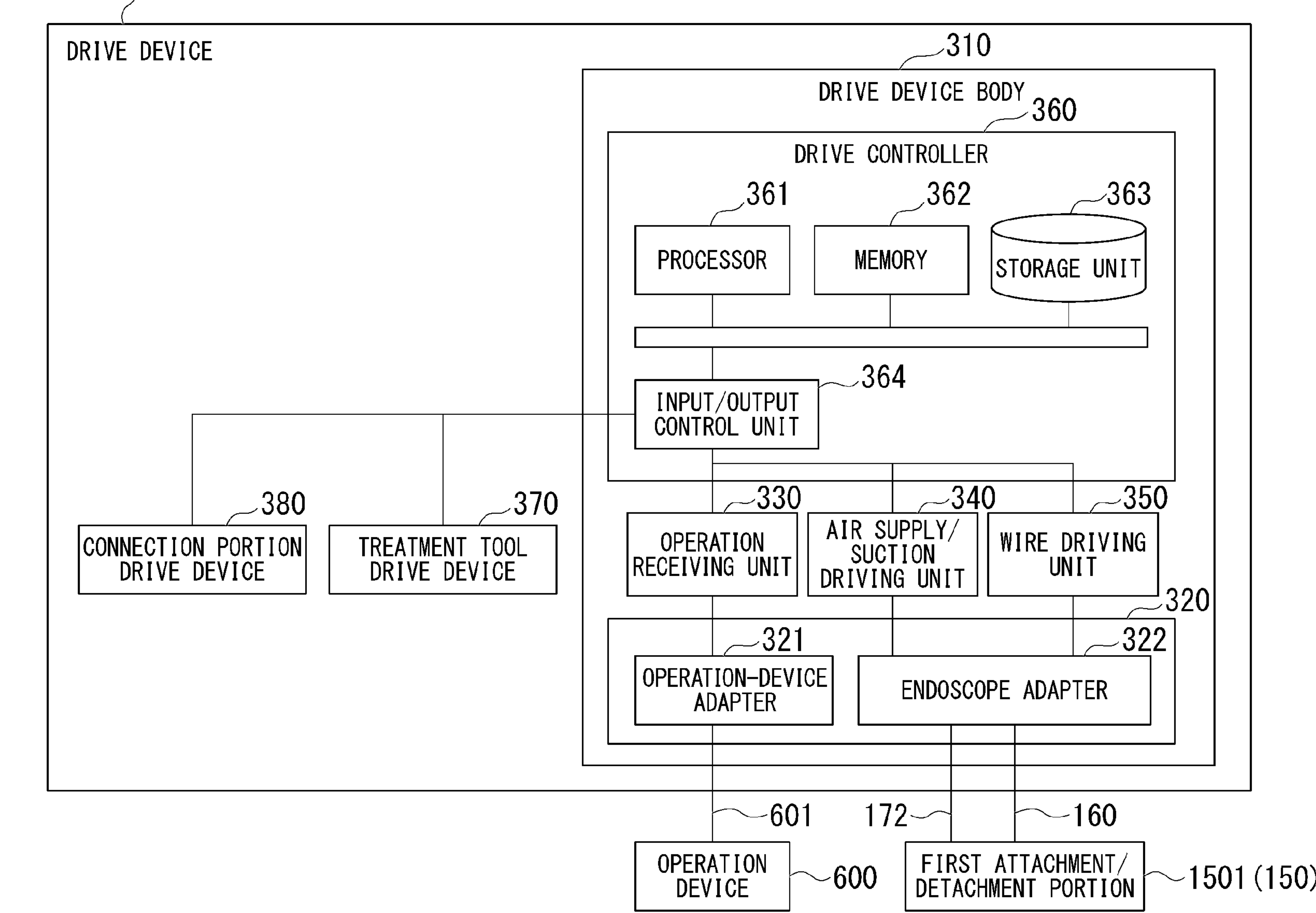
FIG. 4 is a functional block diagram of a drive device of the endoscope system.

FIG. 4 is a functional block diagram of the drive device 300.

The drive device 300 includes a drive device body 310, a treatment tool drive device 370, and a connection portion drive device 380. The drive device body 310 and the treatment tool drive device 370 may be an integrated device. The drive device body 310 and the connection portion drive device 380 may be an integrated device.

The drive device body 310 includes an adapter 320, an operation receiving unit 330, an air supply/suction driving unit 340, a wire driving unit 350, and a drive controller 360.

The adapter 320 includes an operation-device adapter 321 and an endoscope adapter 322. The operation-device adapter 321 is an adapter to which the operation cable 601 is detachably connected. The endoscope adapter 322 is an adapter to which the first attachment/detachment portion 1501 of the endoscope 100 is detachably connected.

The operation receiving unit 330 receives an operation input from the operation device 600 via the operation cable 601. When the operation device 600 and the drive device 300 communicate with each other by wireless communication instead of wired communication, the operation receiving unit 330 includes a known wireless reception module.

The air supply/suction driving unit 340 is connected to the air supply/suction tube 172 inserted into the internal path 101 of the endoscope 100. The air supply/suction driving unit 340 includes a pump and supplies air to the air supply/suction tube 172. The air supply/suction driving unit 340 sucks air from the air supply/suction tube 172.

The wire driving unit 350 includes a drive mechanism including a motor and drives the curved wire 160. Specifically, the wire driving unit 350 drives the operating wire to curve the curved portion 112. The wire driving unit 350 includes an encoder that detects an amount of traction of the curved wire 160. The detected amount of traction is acquired by the drive controller 360.

The drive controller 360 comprehensively controls the drive device 300. The drive controller 360 acquires an operation input received by the operation receiving unit 330. The drive controller 360 controls the air supply/suction driving unit 340, the wire driving unit 350, the connection portion drive device 380, and the treatment tool drive device 370 on the basis of the acquired operation input.

The drive controller 360 includes a processor 361, a memory 362, a storage unit 363 that can store programs and data, and an input/output control unit 364. The drive controller 360 is a computer that can execute a program. The function of the drive controller 360 is realized by causing the processor 361 to execute a program. At least a part of the function of the drive controller 360 may be realized by a dedicated logical circuit.

The input/output control unit 364 is connected to the operation receiving unit 330, the air supply/suction driving unit 340, the treatment tool drive device 370, the connection portion drive device 380, the video control device 400, an input device (not illustrated), and a network device (not illustrated). The input/output control unit 364 performs transmission and reception of data and transmission and reception of a control signal with respect to a device connected thereto under the control of the processor 361.

The drive controller 360 may further include an element in addition to the processor 361, the memory 362, the storage unit 363, and the input/output control unit 364. For example, the drive controller 360 may further include an image computing unit that performs some or all of image processing or image recognition processing.

Since the image computing unit is further provided, the drive controller 360 can perform specific image processing or image recognition processing at a high speed. The image computing unit may be mounted in a separate hardware device connected thereto via a communication line.

The treatment tool drive device 370 is a device to which the operation portion of the endoscopic treatment tool 200 is detachably connected. The treatment tool drive device 370 can operate the operation portion 230 of the endoscopic treatment tool 200 connected thereto on the basis of an instruction from the drive controller 360.

Figure 5:
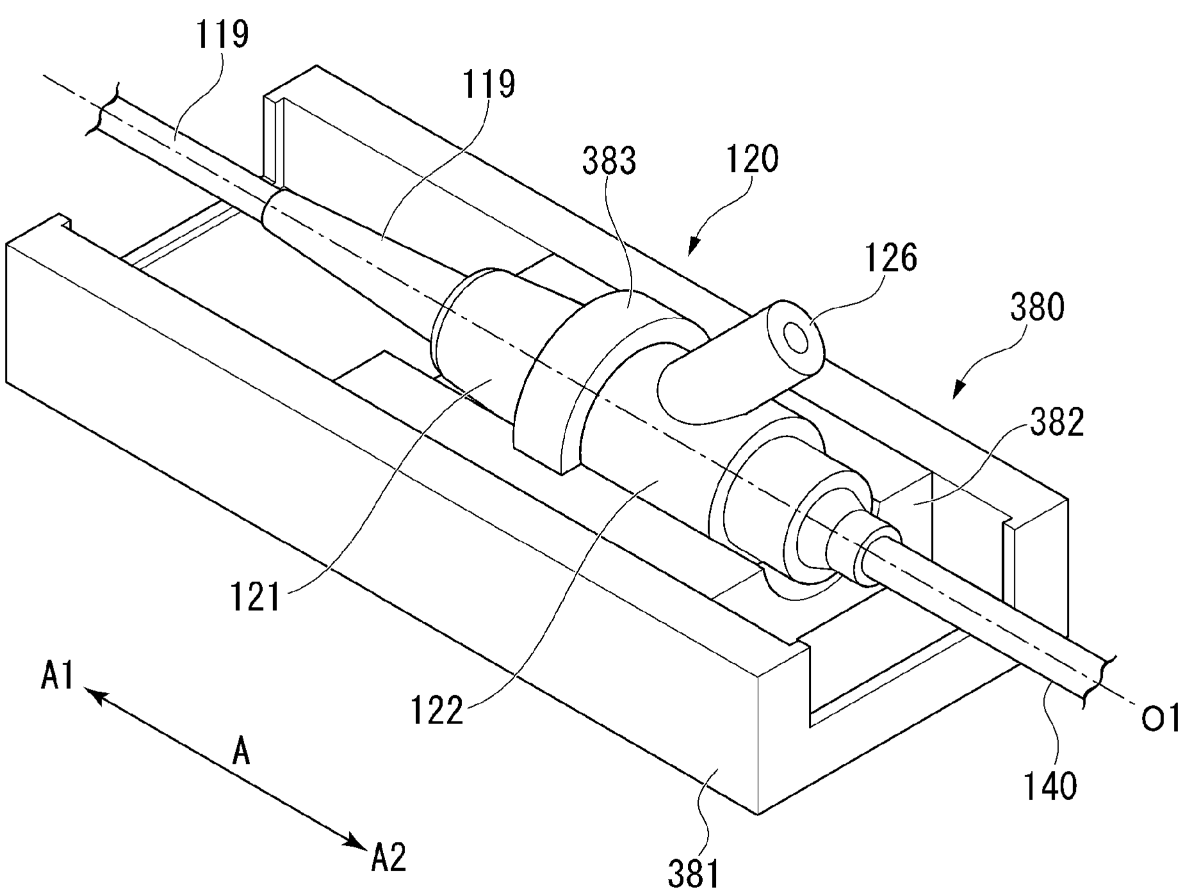
FIG. 5 is a diagram illustrating a connection portion drive device of the drive device.

FIG. 5 is a diagram illustrating the connection portion drive device 380.

The connection portion drive device 380 is a device to which the connection portion 120 of the endoscope 100 is detachably connected. The connection portion drive device 380 can operate the connection portion 120 connected thereto on the basis of an instruction from the drive controller 360.

The connection portion drive device 380 includes a body 381, a advancing/retracting driving unit 382, and a roll-rotation driving unit 383.

The connection portion body 122 of the connection portion 120 is detachably fixed to the advancing/retracting driving unit 382. The advancing/retracting driving unit 382 is driven by a motor or the like and advances and retracts the connection portion body 122 in the length direction A relative to the body 381. The drive controller 360 can advance and retract the insertion portion 110 of the endoscope 100 in the length direction A by driving the advancing/retracting driving unit 382 to advance and retract the connection portion body 122.

The cylindrical member 121 of the connection portion 120 is detachably fixed to the roll-rotation driving unit 383.

The roll-rotation driving unit 383 is driven by a motor or the like to rotate the cylindrical member 121 about the center axis O1 in the length direction A relative to the connection portion body 122 fixed to the advancing/retracting driving unit 382. The drive controller 360 can rotate the insertion portion 110 of the endoscope 100 about the length direction A by driving the roll-rotation driving unit 383 to rotate the cylindrical member 121 relative to the connection portion body 122.

Video Control Device 400

Figure 6:
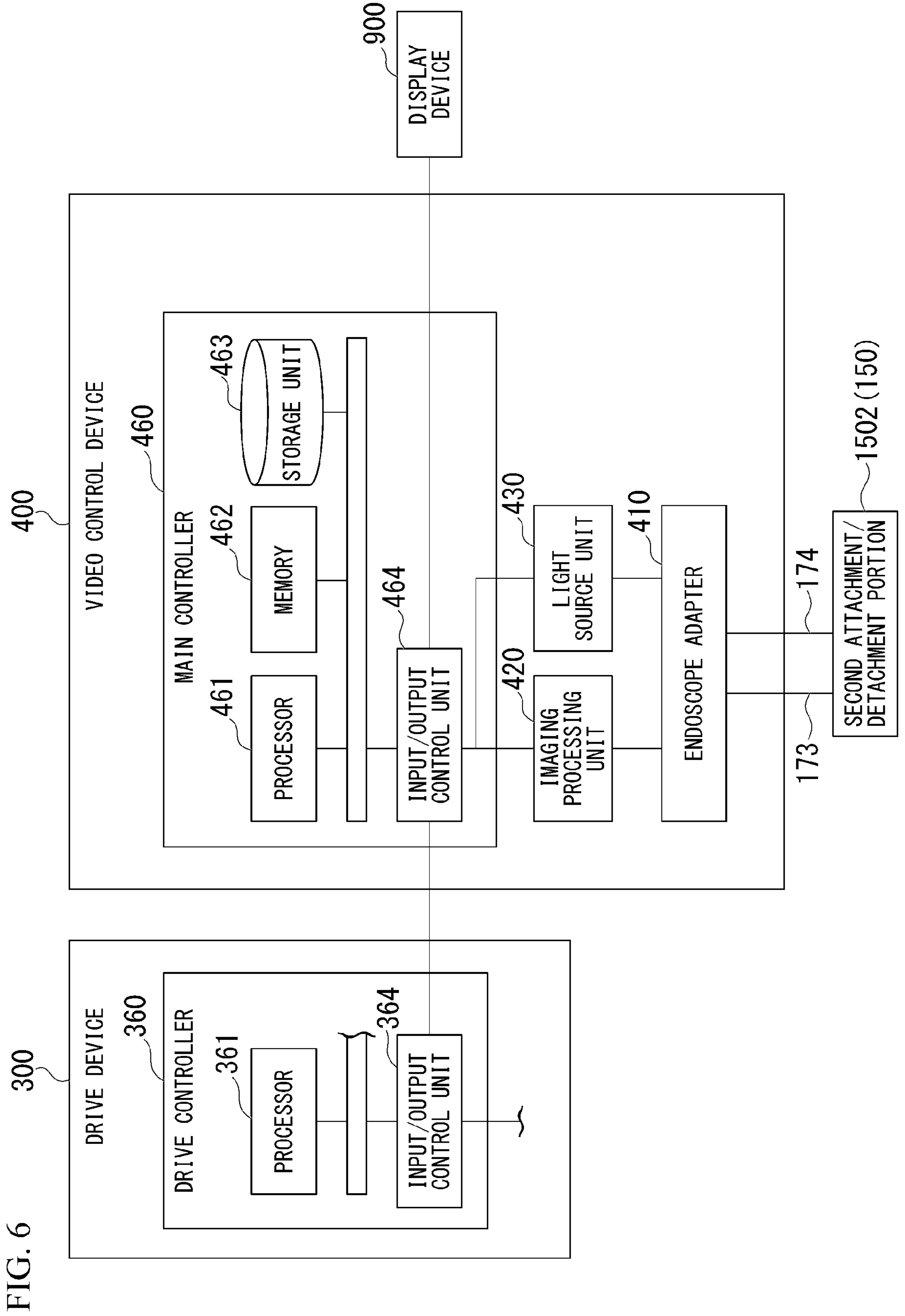
FIG. 6 is a functional block diagram of a video control device of the endoscope system.

FIG. 6 is a functional block diagram of the video control device 400.

The video control device 400 includes an endoscope adapter 410, an imaging processing unit 420, a light source unit 430, and a main controller 460.

The endoscope adapter 410 is an adapter to which the second attachment/detachment portion 1502 of the endoscope 100 is detachably connected.

The imaging processing unit 420 converts an imaging signal acquired from the imaging portion 111*c* of the distal end portion 111 via the imaging cable 173 to a captured image.

The light source unit 430 generates illumination light which is applied to an imaging target. The illumination light generated by the light source unit 430 is guided to the illumination portion 111*b* of the distal end portion 111 via the light guide 174.

The main controller 460 includes a processor 461, a memory 462 that can read programs, a storage unit 463, and an input/output control unit 464. The main controller 460 that can execute a program. The function of the main controller 460 is realized by causing the processor 461 to execute a program. At least a part of the function of the main controller 460 may be realized by a dedicated local circuit.

The storage unit 463 is a nonvolatile recording medium that stores the aforementioned programs or necessary data. The storage unit 463 includes, for example, a ROM or a hard disk. A program recorded in the storage unit 463 is read into the memory 462 and executed by the processor 461.

The input/output control unit 464 is connected to the imaging processing unit 420, the light source unit 430, the drive device 300, the display device 900, an input device (not illustrated), and a network device (not illustrated). The input/output control unit 464 performs transmission and reception of data and transmission and reception of a control signal with respect to a device connected thereto under the control of the processor 461.

The main controller 460 can perform image processing on a captured image acquired by the imaging processing unit 420. The main controller 460 can generate a GUI image or a CG image for providing information to an operator. The main controller 460 can display the captured image, the GUI image, or the CT image on the display device 900.

The main controller 460 is not limited to an integrated hardware device. For example, the main controller 460 may be constituted by separating a part thereof as a separate hardware device and connecting the separated hardware device thereto via a communication line. For example, the main controller 460 may be a cloud system that connects the separated storage unit 463 thereto via a communication line.

The main controller 460 may further include an element in addition to the processor 461, the memory 462, the storage unit 463, and the input/output control unit 464. For example, the main controller 460 may further include an image computing unit that performs some or all of image processing or image recognition processing. Since the image computing unit is further provided, the main controller 460 can perform specific image processing or image recognition processing at a high speed. The image computing unit may be mounted in a separate hardware device connected thereto via a communication line.

Figure 7:
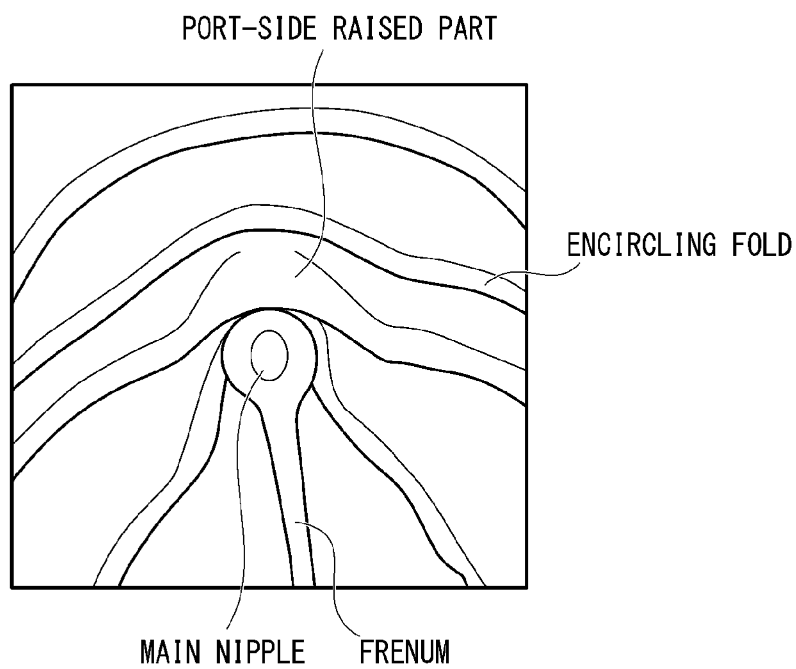
FIG. 7 is a diagram schematically illustrating a shape of a nipple when the nipple is viewed from the front.
Figure 8:
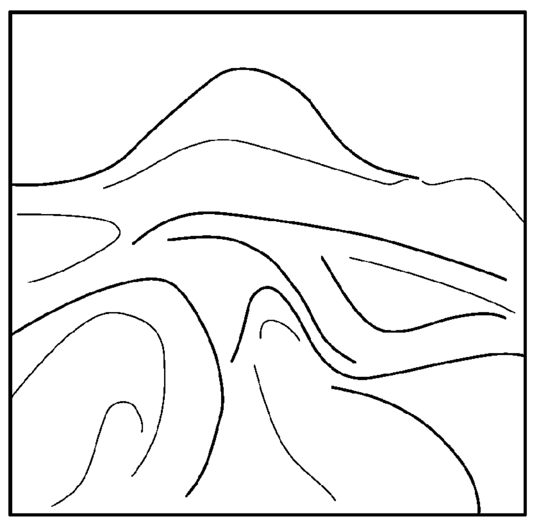
FIG. 8 is a diagram illustrating a shape of a nipple of a patient.
Figure 9:
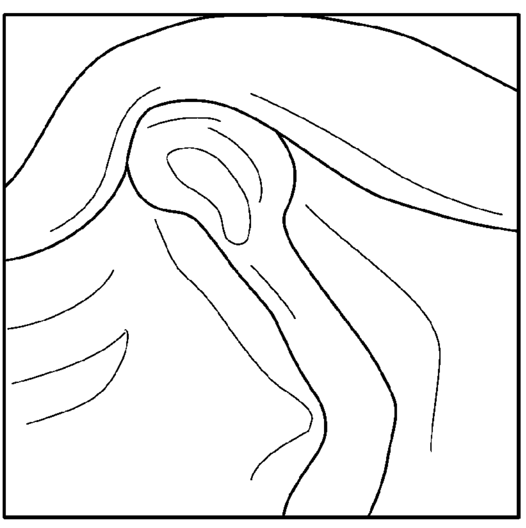
FIG. 9 is a diagram illustrating a shape of a nipple of a patient.
Figure 10:
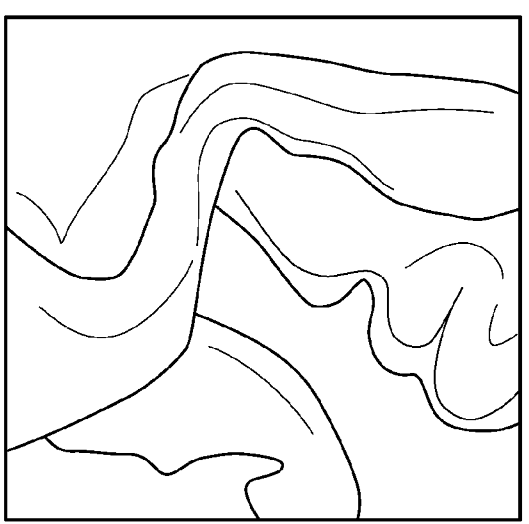
FIG. 10 is a diagram illustrating a shape of a nipple of a patient.
Figure 11:
FIG. 11 is a diagram illustrating a shape of a nipple of a patient.

FIG. 7 is a diagram schematically illustrating a shape of a nipple PA when the nipple PA is viewed from the front.

As illustrated in FIG. 7, a structure specific to the nipple PA is present near a main nipple which is an opening of a biliary duct B. Specifically, structures called a frenum, an encircling fold, and a port-side raised part are present near the main nipple.

FIGS. 8 to 11 are diagrams illustrating a shape of a nipple PA of a patient.

The schematic diagram illustrated in FIG. 7 represents a typical shape of a nipple PA, and the shape of the nipple PA differs between individual patients as illustrated in FIGS. 8 to 11. For example, the shape of the main nipple, the frenum, the encircling fold, and the port-side raised part may not be clear or may be greatly different from the typical shape. An opening of the biliary duct B is often open. In this case, it is difficult to accurately ascertain whether the opening is located with eyes.

Figure 12:
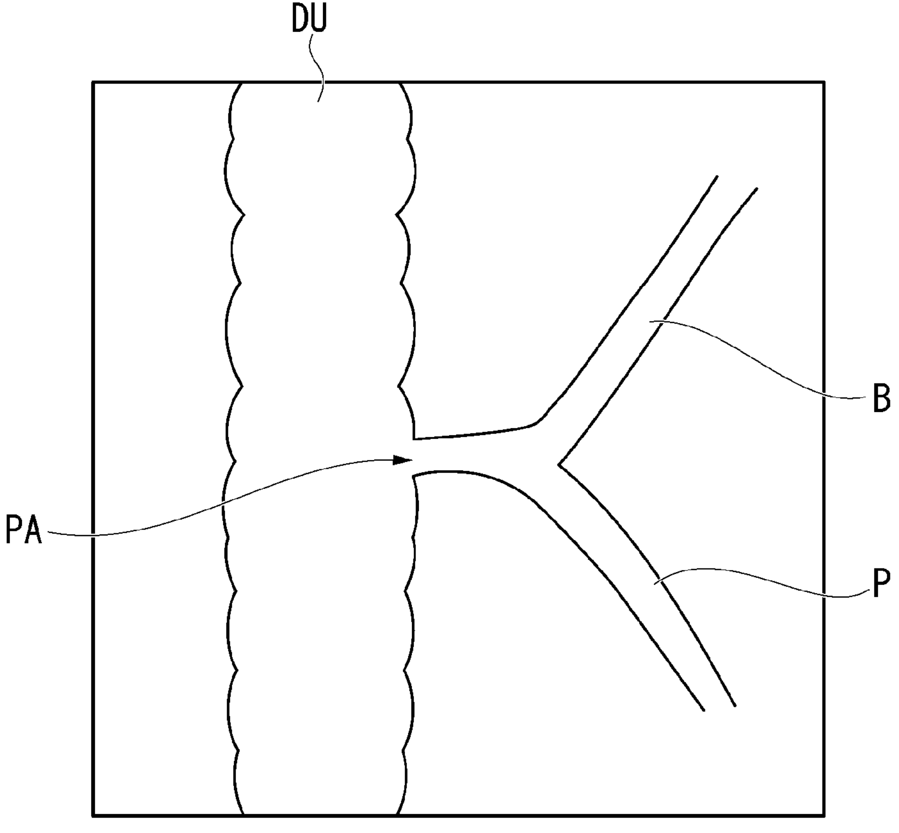
FIG. 12 is a sectional view illustrating a biliary duct, a pancreatic duct and shapes of openings thereof.
Figure 13:
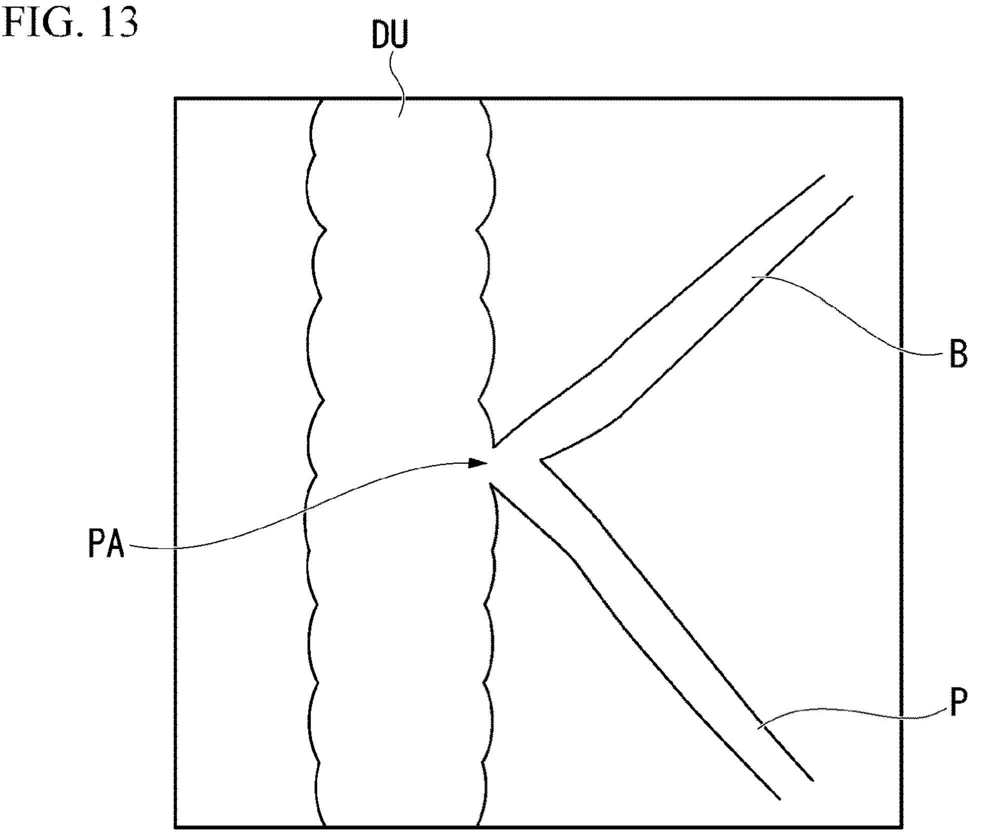
FIG. 13 is a sectional view illustrating a biliary duct, a pancreatic duct and shapes of openings thereof.
Figure 14:
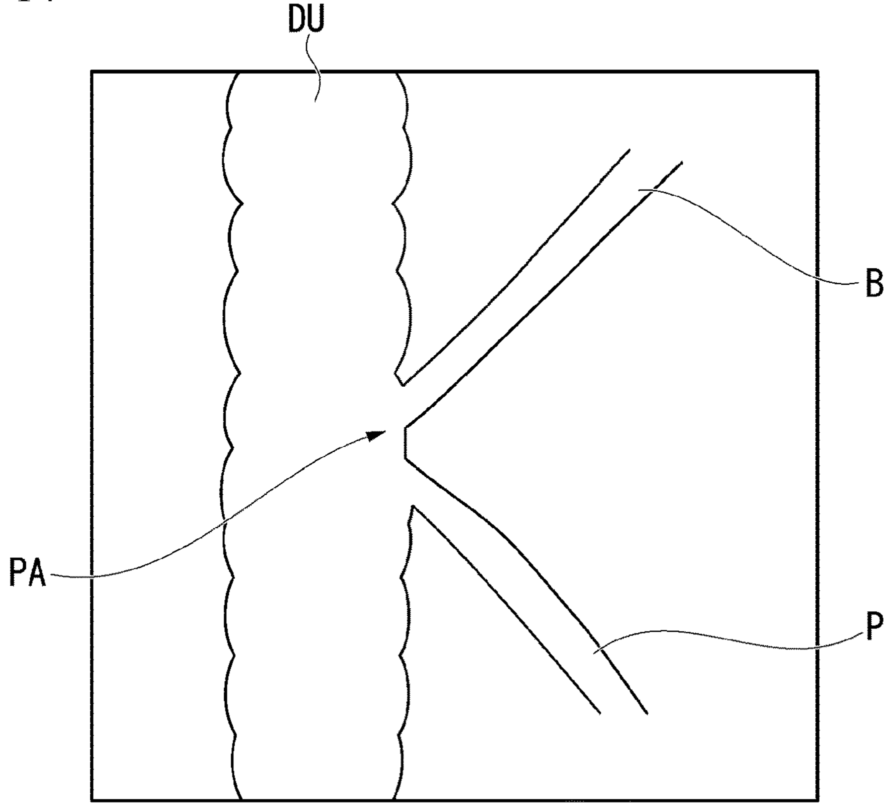
FIG. 14 is a sectional view illustrating a biliary duct, a pancreatic duct and shapes of openings thereof.

FIGS. 12 to 14 are sectional views illustrating shapes of a biliary duct B, a pancreatic duct P, and openings thereof.

The shapes of a biliary duct B, a pancreatic duct P, and openings thereof are classified into type I called a Y-shape (FIG. 12), type II called a V-shape (FIG. 13), and type III called a U-shape or a separated shape (FIG. 14). In type I, the biliary duct B and the pancreatic duct P merge to a common tube at a merging part, and the common tube is open to the nipple PA. In type II, a merging part at which the biliary duct B and the pancreatic duct P merge is open to the nipple, and no common tube is provided. In type III, the biliary duct B and the pancreatic duct P are separately open to the nipple PA, and no merging portion and no common tube are provided. Most patients have type I, but patients having type II or type II are also present. The shape of the biliary duct B can be predicted to a certain extent on the basis of the shape of the nipple PA.

The storage unit 463 stores biliary duct shape information which is information prepared on the basis of past cases, experiences of doctors, and the like and in which a captured image (standard image) of a nipple PA when the nipple PA is viewed from the front and a standard shape of a biliary duct B are correlated. The standard image may include an image such as FIGS. 8 to 11. In other words, the standard image is associated with the standard shape of a biliary duct B. The standard shape may include shapes disclosed in FIGS. 12 to 14. The main controller 460 can predict the shape of the biliary duct B from the captured image of the nipple PA with individual differences on the basis of the biliary duct shape information.

The biliary duct shape information may be prepared by an expert such as a doctor or may be prepared by machine learning.

Operation of Endoscope System 1000

Figure 15:
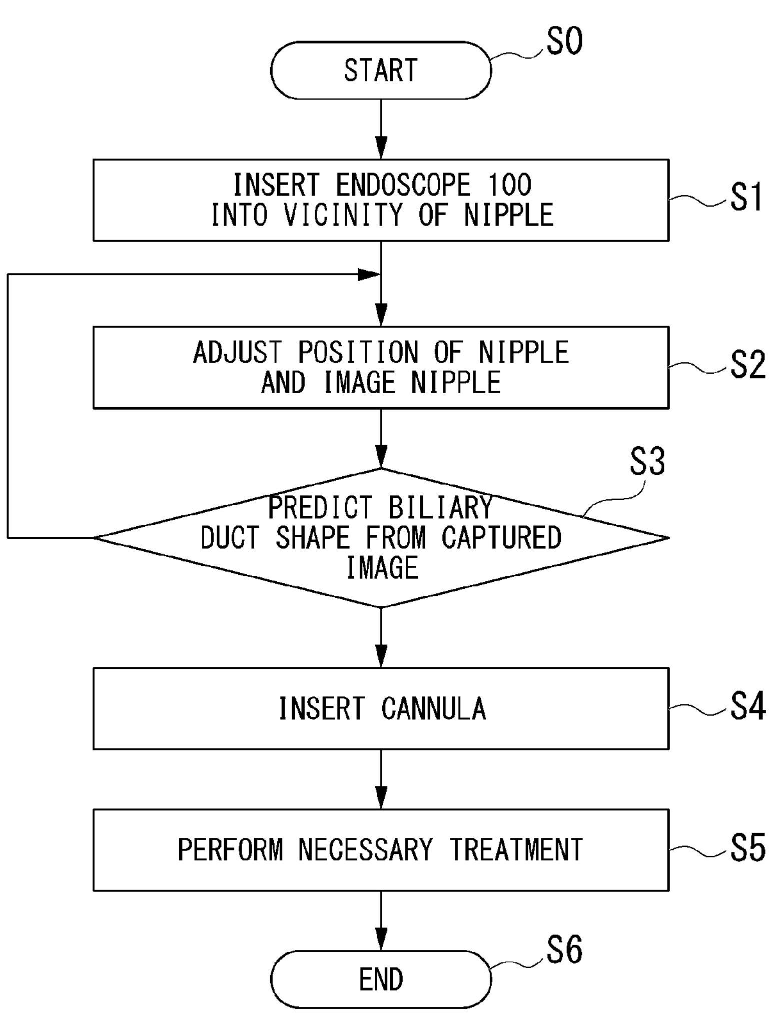
FIG. 15 is a diagram illustrating a control flow which is performed by a main controller and a drive controller.

The operation of the endoscope system 1000 according to this embodiment will be described below. Specifically, a manual operation of endoscopic retrograde cholangiopancreatography (ECRP) will be described. FIG. 15 is a diagram illustrating a control flow which is performed by the main controller 460 (mainly the processor 461) and the drive controller 360 (mainly the processor 361).

Step S1: Endoscope Inserting Step

Figure 16:
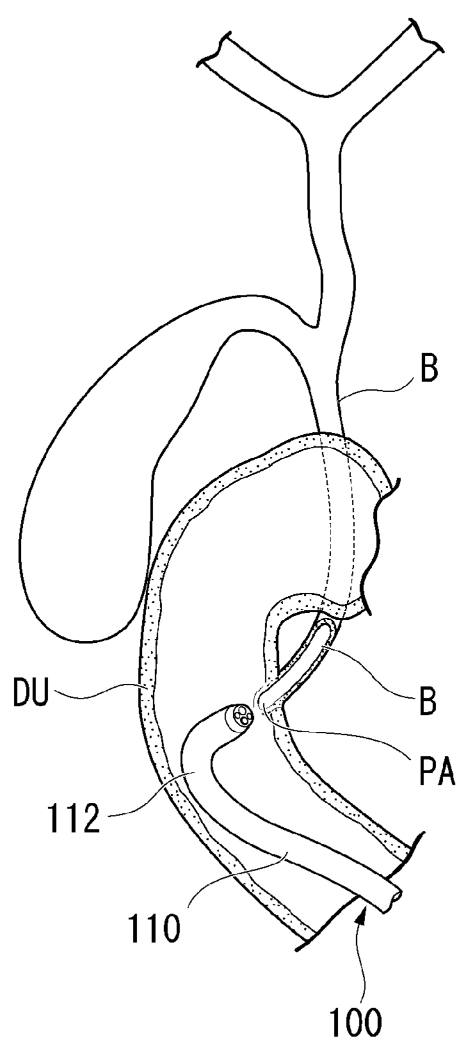
FIG. 16 is a diagram illustrating an endoscope inserting step.

FIG. 16 is a diagram illustrating an endoscope inserting step.

In Step S1, an operator inserts the insertion portion 110 of the endoscope 100 into a lumen of a patient via a natural opening such as an anal passage. The connection portion drive device 380 inserts the distal end portion 111 of the endoscope 100 into the duodenum DU and locates the distal end portion 111 in the vicinity of the nipple PA by advancing or retracting and rolling and rotating the endoscope 100. The wire driving unit 350 operates the operation device 600 to curve the curved portion 112 as needed. For example, the wire driving unit 350 curves the curved portion 112 in a J-shape such that the imaging portion 111*c* is in front of the nipple PA as illustrated in FIG. 16. The endoscope 100 may be manually operated by an operator's hand.

Step S2: Nipple Position Adjusting Step

Figure 17:
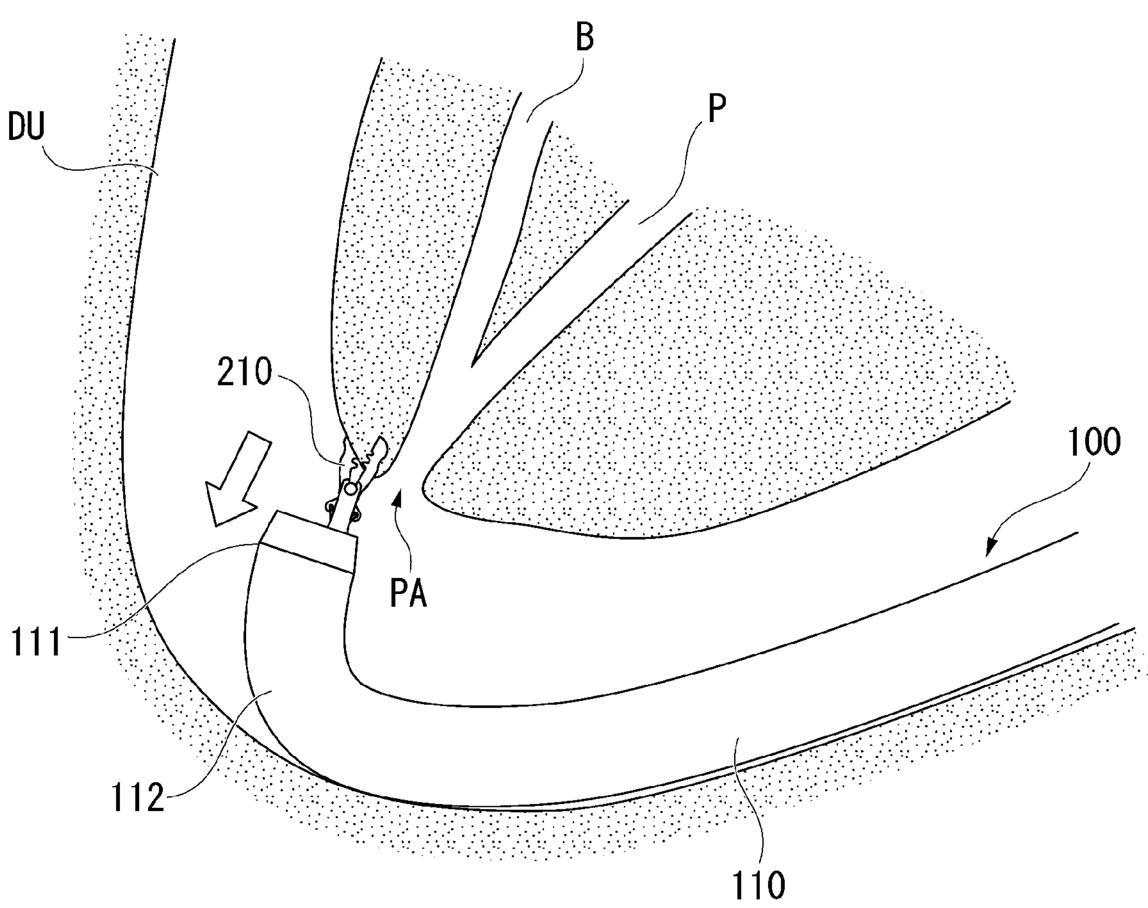
FIG. 17 is a diagram illustrating a nipple position adjusting step.

FIG. 17 is a diagram illustrating a nipple position adjusting step.

In Step S2, the treatment tool drive device 370 operates the operation portion 230 of the endoscopic treatment tool 200 and adjusts the position or direction of the nipple PA using the forceps 210 until a captured image in which the nipple PA is viewed from the front is acquired. Specifically, the treatment tool drive device 370 drives the forceps 210 to move the nipple PA in a state in which the forceps 210 grasps tissue near the nipple PA. The treatment tool drive device 370 moves the nipple PA such that the nipple PA is located, for example, at the center of the captured image.

Until a captured image in which the nipple PA is viewed from the front is acquired, the wire driving unit 350 or the connection portion drive device 380 may adjust the position or direction of the endoscope 100.

The position or direction of the nipple PA may be adjusted using a cannula which is used in subsequent steps instead of the endoscopic treatment tool 200. Specifically, the treatment tool drive device 370 adjusts the position or direction of the nipple PA by operating the cannula inserted into the nipple PA.

The position or direction of the nipple PA may be adjusted using a suction unit, for example the air supply/suction driving unit 340 and the channel tube 171, instead of the endoscopic treatment tool 200. Specifically, the treatment tool drive device 370 adjusts the position or direction of the nipple PA by operating the suction unit holding tissue near the nipple PA by suction.

Step S3: Biliary Duct Shape Predicting Step

In Step S3, the main controller 460 predicts the shape of the biliary duct B connected to the nipple PA in the captured image on the basis of the biliary duct shape information. When the shape of the biliary duct B cannot be predicted from the captured image of the nipple PA, the main controller 460 performs the nipple position adjusting step of Step S2 again and acquires another captured image. For example, the main controller 460 compares the captured image of the nipple PA with the standard image, determines the most similar image among the standard images to the captured image, and use the standard shape that is associated with the most similar image for predicting the shape of the biliary duct B. The main controller 460 may determine the most similar image by calculating a degree of similarity between the captured image and the standard image.

Step S4: Cannula Inserting Step

The operator pulls out the endoscopic treatment tool 200 from the channel tube 171 and inserts a cannula into the channel tube 171. The cannula is driven by the treatment tool drive device 370 similarly to the endoscopic treatment tool 200. The treatment tool drive device 370 inserts the cannula into the biliary duct B on the basis of the predicted shape of the biliary duct B in Step S4.

Step S5: Treatment Step

The main controller 460 drives the treatment tool drive device 370 to perform a manual operation of endoscopic retrograde cholangiopancreatography (ECRP).

With the endoscope system 1000 according to this embodiment, it is possible to easily ascertain a nipple of a biliary duct from the front of a direct-view flexible endoscope. Accordingly, it is possible to ascertain the nipple PA from the front to acquire a captured image and to easily predict the shape of the biliary duct B connected to the nipple PA in the captured image on the basis of the biliary duct shape information.

While the first embodiment of the present disclosure has been described above in details with reference to the drawings, a specific configuration is not limited to this embodiment and includes a change in design without departing from the gist of the present disclosure. Elements described in the aforementioned embodiment and following modified examples can be appropriately combined into a configuration.

The present disclosure can be applied to a manual operation of endoscopic retrograde cholangiopancreatography (ECRP).

What is claimed is:

1. An endoscope system comprising:
- a forward-view endoscope configured to capture images;
- a treatment tool inserted into the forward-view endoscope; and
- a controller comprising hardware, the controller being configured to:
  - control a drive device to drive the forward-view endoscope to a vicinity of a duodenal papilla within a lumen,
  - control the drive device to drive the treatment tool to move the duodenal papilla to a position,
  - acquire, from the forward-view endoscope, an image of the duodenal papilla at the position, and
  - predict, based on the image and reference images of duodenal papillae with corresponding shapes of biliary ducts, a shape of a biliary duct connected to the duodenal papilla.

2. The endoscope system according to claim 1, wherein the controller is further configured to, prior to controlling the drive device to drive the treatment tool to move the duodenal papilla to the position:
- control the drive device to drive the treatment tool to move the duodenal papilla to another position,
- acquire, from the forward-view endoscope, another image of the duodenal papilla at the other position, and
- determine that the shape of the biliary duct cannot be predicted based on the other image,
- wherein the controlling the drive device to drive the treatment tool to move the duodenal papilla to the position, the acquiring the image of the duodenal papilla, and the predicting the shape of the biliary duct are responsive to determining that the shape of the biliary duct cannot be predicted based on the other image.

3. The endoscope system according to claim 1, wherein the controller is further configured to control driving of a cannula into the biliary duct based on the predicted shape of the biliary duct.

4. The endoscope system according to claim 1, wherein: the treatment tool are forceps, and the driving of the treatment tool comprises operating the forceps to grasp the duodenal papilla.

5. The endoscope system according to claim 1, wherein: the treatment tool is a cannula, and the driving of the treatment tool comprises inserting the cannula into the duodenal papilla.

6. The endoscope system according to claim 1, wherein: the treatment tool is a suction unit, and the driving of the treatment tool comprises operating the suction unit to hold the duodenal papilla by suction.

7. A method of treating a biliary duct, the method comprising:

locating an endoscope in a vicinity of a duodenal papilla of the biliary duct;

moving the duodenal papilla to a position using a treatment tool attached to the endoscope;

acquiring, from the endoscope, an image of the duodenal papilla at the position; and predicting, based on the image an reference images of duodenal papillae with corresponding shapes of biliary ducts, a shape of the biliary duct.

8. The method according to claim 7, further comprising, prior to moving the duodenal papilla to the position:

moving the duodenal papilla to another position using the treatment tool, acquiring, from the endoscope, another image of the duodenal papilla at the other position, and determining that the shape of the biliary duct cannot be predicted based on the other image, wherein the moving the duodenal papilla to the position, the acquiring the image of the duodenal papilla, and the predicting the shape of the biliary duct are responsive to determining that the shape of the biliary duct cannot be predicted based on the other image when.

9. The method according to claim 7, further comprising inserting a cannula into the biliary duct based on the predicted shape of the biliary duct.

10. The method according to claim 7, wherein the treatment tool are forceps, and the moving the duodenal papilla to the position comprises using the forceps to grasp the duodenal papilla.

11. The method according to claim 7, wherein the treatment tool is a cannula, and the moving the duodenal papilla to the position comprises inserting the cannula into the duodenal papilla.

12. The method according to claim 7, wherein the treatment tool is a suction unit, and the moving the duodenal papilla to the position comprises using the suction unit to hold the duodenal papilla by suction.

13. The method according to claim 7, wherein the endoscope is a forward-view endoscope.

* * * * *